US009468210B2

(12) United States Patent
Ramalingam et al.

(10) Patent No.: US 9,468,210 B2
(45) Date of Patent: Oct. 18, 2016

(54) COMPOSITIONS FOR POST-HARVEST TREATMENT AND RELATED METHODS

(71) Applicant: Syngenta Participations AG, Basel (CH)

(72) Inventors: Nagarajan Ramalingam, Greensboro, NC (US); David Charles Ross, Greensboro, NC (US); Matthew Robert Cottle, Greensboro, NC (US); Eric Stephen Oshige, Greensboro, NC (US); Gabriel Ian Oxby, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/898,556

(22) PCT Filed: Jun. 16, 2014

(86) PCT No.: PCT/US2014/042451
§ 371 (c)(1),
(2) Date: Dec. 15, 2015

(87) PCT Pub. No.: WO2014/204822
PCT Pub. Date: Dec. 24, 2014

(65) Prior Publication Data
US 2016/0150781 A1    Jun. 2, 2016

Related U.S. Application Data

(60) Provisional application No. 61/836,583, filed on Jun. 18, 2013.

(51) Int. Cl.
*A01N 43/36* (2006.01)

(52) U.S. Cl.
CPC .................................... *A01N 43/36* (2013.01)

(58) Field of Classification Search
CPC ....................................................... A01N 43/36
USPC ....................................................... 514/422
See application file for complete search history.

(56) References Cited

U.S. PATENT DOCUMENTS

| 4,857,345 A | 8/1989 | Sardo |
| 4,990,351 A | 2/1991 | Orman et al. |
| 5,858,436 A | 1/1999 | Bompeix et al. |
| 6,723,364 B1 | 4/2004 | Bompeix et al. |
| 8,173,681 B2 | 5/2012 | Steiner et al. |
| 8,252,719 B2 | 8/2012 | Douglass et al. |
| 2003/0118705 A1 | 6/2003 | Cook et al. |
| 2004/0071797 A1 | 4/2004 | Dennis et al. |
| 2005/0031744 A1 | 2/2005 | Paliyath et al. |
| 2005/0084573 A1 | 4/2005 | Gorton et al. |
| 2005/0123528 A1 | 6/2005 | Gorton et al. |
| 2008/0016766 A1 | 1/2008 | Sardo |
| 2008/0103212 A1 | 5/2008 | Wartanessian |
| 2008/0175926 A1 | 7/2008 | Bompeix et al. |
| 2008/0261811 A1 | 10/2008 | Krohn et al. |
| 2009/0018194 A1 | 1/2009 | Garcia-Pareja et al. |
| 2010/0123018 A1 | 5/2010 | Sardo |
| 2010/0298139 A1 | 11/2010 | Suty-Heinze et al. |
| 2011/0034496 A1 | 2/2011 | Hauser-Hahn et al. |

FOREIGN PATENT DOCUMENTS

| EP | 669078 | 8/1995 |
| EP | 0972450 | 1/2000 |
| EP | 1946642 | 7/2008 |
| WO | 98/31229 | 7/1998 |
| WO | 00/05969 | 2/2000 |
| WO | 00/49880 | 8/2000 |
| WO | 03/007723 | 1/2003 |
| WO | 03/051143 | 6/2003 |
| WO | 2009/123744 | 10/2009 |
| WO | 2011/124586 | 10/2011 |
| WO | 2013/011108 | 1/2013 |

OTHER PUBLICATIONS

Vectorfog. "What is ULV?" Publication [online]. Dec. 12, 2012 (retrieved on Aug. 27, 2014). Retrieved from the Internet: ULF: https://web.archive.org/web/20121212073142/http://www.vectorfog.com/what-is-ulv>.
The Dow Chemical Company, "Dow P-Series Glycol Ethers." Publication [online]. Jul. 2002 (retrieved on Aug. 27, 2014). Retrieved from the internet: URL: http://msdssearch.dow.com/PublishedLiteratureDOWCOM/dh_012d/0901b8038012d976.pdf?filepath=oxysolvents/pdfs/moreg/110-00977.pdf&fromPage=GetDoc>. p. 1, row5.
International Search Report for International Patent Application No. PCT/US2014/42451 mailed Oct. 10, 2014.

*Primary Examiner* — Taofiq A Solola
(74) *Attorney, Agent, or Firm* — R. Kody Jones

(57) ABSTRACT

Novel compositions and methods for the post-harvest treatment of crops are disclosed and described. In one example, a composition includes a fungicidally-active compound, an ether solvent, and a filler. In many embodiments, the composition is ready-to-fog.

16 Claims, 2 Drawing Sheets

COMPOSITIONS FOR POST-HARVEST TREATMENT AND RELATED METHODS

RELATED APPLICATION INFORMATION

Figure 1:
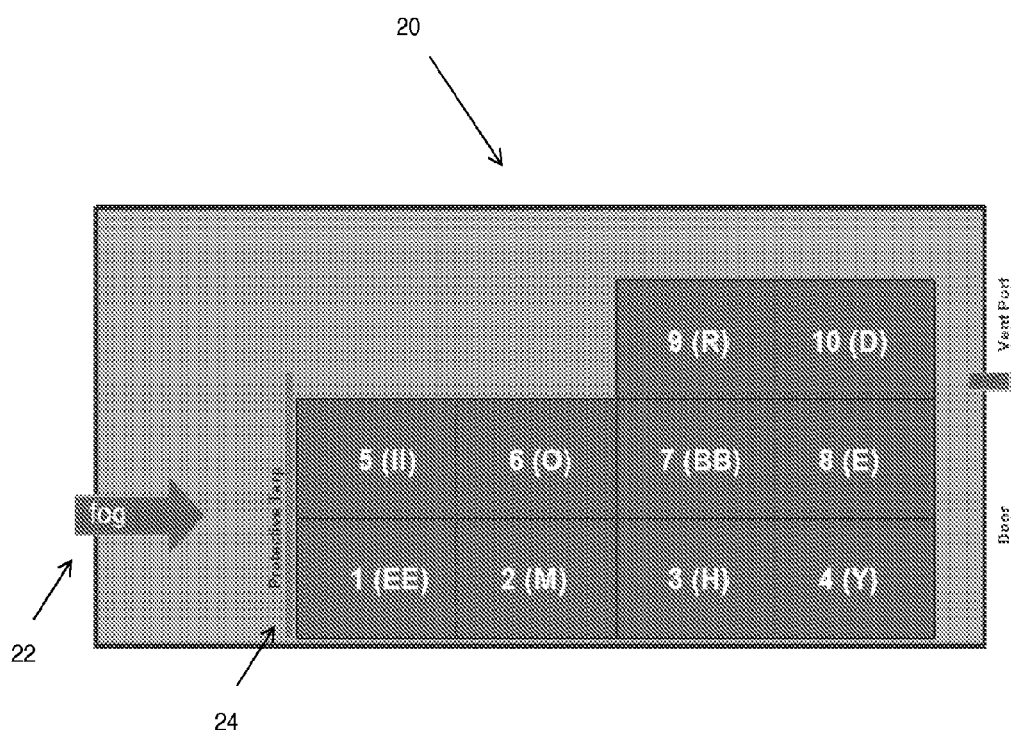

This application is a 371 of International Application No. PCT/US2014/042451, filed 16 Jun. 2014, which claims priority to U.S. Provisional Application No. 61/836,583, filed 18 Jun. 2013, the contents of which are incorporated by reference herein.

FIELD OF THE TECHNOLOGY

The present disclosure relates generally to treatment of harvested crops, and more particularly to compositions and methods for treating post-harvested crops.

BACKGROUND

Applicants consider crop loss, e.g. in the supply chain, to be a serious problem around the world. As a result, applicants desire, inter alia, improved compositions and methods for post-harvest treatments to reduce crop loss. By way of example, applicants desire compositions and methods that provide any number of benefits including at least one of improved disease control, increased storage life, improved application uniformity, improved application safety and reduced phytotoxicity.

Further, applicants desire compositions that are suitable for thermal fogging applications, and even more particularly, compositions that are ready-to-fog (RTF) for application by thermal fogging. Existing fogging techniques, by way of contrast, often require combining an active ingredient (ai) into a carrier such as propylene glycol or diphenylamine, usually with the addition of a heating step (e.g. to 180-190° F.) to dissolve the ai. Other traditional fogging typically uses diesel, crop oils, isopropanol, methanol, etc.

While generally effective, applicants believe existing technologies have the potential to suffer from any number of problems including: handling, storage and shipping of the ai in what is basically a technical form; operator error around accurately measuring the ai; insuring uniform mixing of the ai within the carrier; and the requirement for procuring and maintaining additional equipment to heat, pump and inject slurries to be fogged to the thermal fogger.

Various embodiments may address any number of these, or additional, problems.

SUMMARY

The current disclosure is directed to, inter alia, compositions and methods for treating post-harvest crops. In one embodiment, the disclosure includes about 1% to about 20%, by weight percent, of at least one fungicidally-active compound; about 1% to about 80%, by weight percent, of at least one ether solvent; and about 20% to about 35%, by weight percent, of at least one filler. Fungicidally-active compounds may vary. In some examples, the fungicidally active compound includes at least one of fludioxonil, mefenoxam, difenoconazole, propiconazole, and azoxystrobin. Further, in some embodiments, compositions will comprise less than about 1%, by weight percent, of aqueous carrier, e.g. water.

In another embodiment, the disclosure includes applying a composition, e.g. as described above, to a harvested fruit or vegetable. In many examples, the application will include fogging the composition. Further, in many examples, the composition will be configured as a ready-to-fog (RTF) compositions for fogging applications.

The above summary was intended to summarize certain embodiments of the present disclosure. Embodiments will be set forth in more detail in the tables and description below. It will be apparent, however, that the particular description of specific embodiments is not intended to limit the scope of the present inventions.

DESCRIPTION OF EXEMPLARY EMBODIMENTS

As introduced above, it will be understood that composition and method details herein are for the purpose of describing embodiments of the disclosure and are not intended to limit the disclosure or any invention thereto.

Generally, the disclosure provides compositions and methods of using and making a composition for post-harvest treatment. In some embodiments, compositions include a fungicidally-active compound; an ether solvent; and a filler.

The term fungicidally-active compound as utilized herein includes compounds active against phytopathogenic fungi. Compounds may include compounds in any number of classes, for example, triazole derivatives, strobilurins, carbamates (including thio- and dithiocarbamates), benzimidazoles (thiabendazole), N-trihalomethylthio compounds (captan), substituted benzenes, carboxamides, phenylamides, phenylpyrroles, and succinate dehydrogenase inhibitors.

Suitable triazole derivatives may include propiconazole, difenconazole, tebuconazole, tetraconazole and triticonazole. Suitable strobilurins include trifloxystrobin, azoxystrobin, kresoxim-methyl, pyraclostrobin, and picoxystrobin. In other examples, suitable carbamates include thiram. Suitable substituted benzenes include PCNB and chlorothalonil. Suitable carboxamides include carboxin. Suitable phenylamides include metalaxyl; metalaxyl consisting of more than 70% by weight of the R-enantiomer; metalaxyl consisting of more than 85% by weight of the R-enantiomer; metalaxyl consisting of more than 92% by weight of the R-enantiomer; metalaxyl consisting of more than 97% by weight of the R-enantiomer; and mefenoxam (i.e., R-metalaxyl or metalaxyl-M). Suitable succinate dehydrogenase inhibitors include benzovindiflupyr.

Other suitable fungicidally-active compounds may include benomyl (also known as benlate), bitertanol, carbendazim, capropamid, cymoxanil, cyprodinil, ethirimol, fenpiclonil, fenpropimorph, fluquinconazole, flutolanil, flutriafol, fosetyl-aluminum, fuberidazole, guazatine, hymexanol, kasugamycin, imazalil, imibenconazole, iminoctadine-triacetate, ipconazole, iprodione, mancozeb, maneb, mepronil, metconazole, metiram, myclobutanil, nuarimol, oxadixyl, oxine-copper, oxolinic acid, pefurazoate, pencycuron, prochloraz, propamocarb hydrochloride, pyroquilon, silthiopham, tecnazene, thifluzamide, thiophenate-methyl, tolclofos-methyl, triadimenol, triazoxide and triflumizole.

In some embodiments, the fungicidally-active compound may include a combination of compounds. In one example, a mixture of fungicidally-active compounds includes fludioxonil and thiabendazole. In another example, a mixture of fungicidally-active compounds includes fludioxonil and azoxystrobin. In another example, a mixture of fungicidally-active compounds includes fludioxonil and propiconazole. In another example, a mixture of fungicidally-active compounds may include fludioxonil, mefenoxam and difenoconazole. In another example, a mixture of fungicidally-active compounds includes fludioxonil, mefenoxam, difenoconazole, and azoxystrobin.

It should also be clear that fungicidally active compounds include those compounds that are room temperature (25° C.) solid and those compounds that are room temperature liquid.

The amount of fungicidally-active compound may vary from embodiment to embodiment. In typical embodiments, the fungicidally-active compound represents about 1% to about 30% by weight of the composition. Still in some examples, the fungicidally-active compound may represent at least one of the following, about 1% to about 25% by weight of the composition; about 1% to about 20% by weight of the composition; about 1% to about 15% by weight of the composition; about 1% to about 10% by weight of the composition; and about 1% to about 5% by weight of the composition.

In some embodiments, compositions may include an ether solvent. Ether solvents may vary from example to example. In many examples, the ether solvent will have a boiling point in the range of 130° C. to 200° C. and a flash point in the range of 25° C. to 100° C. In some examples, ether solvents will have a boiling point in the range of 130° C. to 155° C. and a flash point in the range of 25° C. to 40° C. Exemplary, ether solvents include glycol ether solvents, including propylene glycol methyl PM ether (e.g. 1-methoxy-2-propanol) such as DOWANOL PM available from the Dow Chemical Company. Other potential ether solvents include Dowanol DPM, Methyl Carbitol, Butyl Carbitol, and Butyl Cellosolve all available from the Dow Chemical Company.

The amount of ether solvent may vary from embodiment to embodiment. In typical embodiments, the ether solvent represents about 1% to about 80% by weight of the composition. Still in some examples the ether solvent may represent at least one of the following, about 20% to about 80% by weight of the composition; about 30% to about 80% by weight of the composition; about 40% to about 80% by weight of the composition; about 50% to about 80% by weight of the composition; and about 60% to about 75% by weight of the composition. In many examples the ether solvent will represent about 70% by weight of the composition.

In some embodiments, compositions may contain additional fillers, for example, to increase the stability of the concentrated formulation and/or increase efficacy of the applied product, particularly during a fogging application to post-harvested crops. Fillers suitable for use may include at least one of 2-ethyl-1-hexanol, alpha-tocopherol, amyl acetate, decyl alcohol, dimethylformamide, dimethylsulfoxide, dipropylene glycol, ethylene glycol, glycerine, hexanol, isopropyl myristate, methyl isobutyl ketone, methyl oleate, N-methyl pyrrolidinone, octanol, oleic acid, oleyl alcohol, propylene glycol, p-xylene, triacetin. Others may prefer other fillers.

Filler amounts may vary, e.g. from about 5% to about 50% by weight of the treating composition; from about 5% to about 45% by weight of the treating composition; from about 5% to about 40% by weight of the treating composition; from about 5% to about 35% by weight of the treating composition; from about 5% to about 30% by weight of the treating composition; from about 5% to about 25% by weight of the treating composition; from about 5% to about 20% by weight of the treating composition; from about 5% to about 15% by weight of the treating composition; and from about 8% to about 12% by weight of the treating composition.

Certain composition embodiments as disclosed herein are particularly suitable for thermal fogging applications, and even more particularly, in many embodiments, as ready-to-fog (RTF) compositions for thermal fogging application. As used herein, RTF compositions include compositions that do not require at least one of: a dilution prior to thermal fogging or a combination of active ingredient (e.g. by melting, heating or otherwise) to a carrier prior to fogging. As such, in many examples, RTF compositions disclosed herein may be contained within a storage and shipping container, and ready for fogging upon opening the storage and shipping container.

Exemplary thermal fogging devices for application by thermal fogging include devices available from IGEBA, e.g. the TF-35, and devices available from XEDA, e.g. the ELECTROFOG. Other thermal foggers include those manufactured by Igeba, Swingtec, and Electrogen, for example. Some may also prefer to build their own thermal fogger, using any combination of propane and electricity as a power supply. Fogging temperatures can range from about 500° F. to about 750° F. More typically, fogging temperatures will range from about 550° F. to about 725° F., and about 600° F. to about 700° F.

The compositions may be used to create a fog having a variety of particle sizes for uniform distribution during application of the active ingredient. In many embodiments, compositions contained herein were able to create a particle size that created unexpected performance. For example, compositions may create fog having a particle size volume median diameter (VMD) in the range of about two to about twenty microns. In many examples, compositions may create fog having a particle size VMD in the range of about three to about ten microns. Particle sizes achievable by the instant disclosure, particularly particle sizes of about five to about ten microns, allowed for excellent distribution of the active ingredient within a bin of post harvested crop. Uniform distribution of active ingredient even in a fully-loaded and stacked bin, including good distribution to the bottom and middle of bins, was achievable. Particle size VMD may be determined using a Sympatec HELOS laser diffraction sensor at approximately 1 meter from the exit of the fogger.

Somewhat similarly, compositions used herein can be fogged to create an application rate in at least one of the following ranges: about 0.1 to about 10 grams of ai per bin, about 0.1 to about 8 grams of ai per bin, about 0.1 to about 5 grams of ai per bin, about 0.1 to about 3 grams of ai per bin, and about 0.25 to about 1 gram of ai per bin. As used herein, per bin is also considered inclusive of 49,600±20 $inches^3$ volume of post-harvest material because in some examples fogging may occur in the absence of an actual bin, e.g. when stored post-harvest material is stored in piles, such as sugar beets. In many examples, however, particularly pome fruit such as apples, the post-harvest material will be contained in bins. The bins may further include a plurality of ventilation slots in the sides and base to promote air flow. One exemplary bin includes the MacroBin 26 Series from Macro Plastics, having approximately 49,600±$inches^3$ of volume capacity. MacroBin 26 further includes approximately 600 ventilation slots, the slots having 1¾"×5⁄16 dimensions on the sides of the bin and 1¼×5⁄16 dimensions in the base of the bin.

In some examples, fillers may be used to increase the visibility of the composition upon fogging. Applicants believe increasing the visibility of the fogged composition may provide any number of benefits, including for example at least one of decreasing applicator exposure to a fogged composition or increasing contact of the fogged composition with post harvested crops. For example, compositions may be fogged to create a visibility when measured by obscuration of light in the range of at least one of 20 to 70% Copt; 25 to 65% Copt; 30 to 60% Copt; 35 to 55% Copt; and 40 to 50% Copt. Copt measurements may be taken using Sympatec HELOS laser diffraction sensor at approximately 1 meter from the exit of the fogger.

Compositions as disclosed herein may also include other inert additives. Such additives include thickeners, flow enhancers, wetting agents, antifoaming agents, biocides, buffers, lubricants, drift control agents, deposition enhancers, adjuvants, evaporation retardants, freeze protecting agents, stabilizing metal salts or hydroxides, UV protecting agents, fragrances, and the like.

Embodiments also include the methods of treating post-harvest fruits or vegetables, for example, by applying the compositions disclosed herein. As noted, preferred application methods will include application by thermal fogging, e.g. as described above.

Application methods may vary, however, including, for example, spraying, drenching, soaking, etc. In many examples, application methods will include fogging the composition.

In many embodiments, target crops to be protected may include any variety of fruit or vegetable. Exemplary post-harvest material includes apples, pears, plums, grapes, peaches, almonds, cherries, strawberries, raspberries, blackberries, bananas, spinach, lettuce, asparagus, cabbages, carrots, onions, tomatoes, potatoes, sugar beets, paprika, beans, lentils, peas, soybeans, marrows, cucumbers, melons, oranges, lemons, limes, grapefruit, mandarins, etc. It should be apparent that this listing does not represent any limitation of targeted crops.

The following examples illustrate some of the aspects of the invention but are not intended to limit its scope.

EXAMPLE 1

Preparation of Test Material

Test compositions were prepared by mixing ingredients as disclosed in Table 1 until a uniform mixture was obtained. FDL=fludioxonil. Concentrations are by weight % unless indicated otherwise.

TABLE 1

|  | Comp. 1 | Comp. 2 | Comp. 3 | Comp. 4 | Comp. 5 |
| --- | --- | --- | --- | --- | --- |
| AI | 10% FDL | 10% FDL | 10% FDL | 10% FDL | 15% FDL |
| Solvent | 80% Dowanol DPM | 80% Dowanol PM | 85% Dowanol DPM | 60% Dowanol DPM | 85% Dowanol DPM |
| Filler | 10% Oleic Acid | 10% Oleic Acid | 5% Oleic Acid | 30% Oleic Acid | na |

EXAMPLE 2

Phytotoxicity Test

Phytotoxicity tests for the test composition were performed to determine how damaging the test composition was to post-harvest material. Sprays were applied in a lab scale spray booth using 110015VK 0.15 GPM Teejet nozzle, 50 psi, at 2 and 4 mph speeds. Organic Pome fruit (Gala, Fuji, and Red Delicious apples and Bartlett and Bosc pears) were sprayed with Composition 1 and Composition 2 above. The phytotoxicity was observed at 2 hours and then at 24 hours.

Damage levels, even at higher application rates (such as estimated to be 20× fogging application rates), were found to be within commercially acceptable ranges.

EXPERIMENT 3

Fogging

Test composition 2 was fogged using an Igeba TF-35 thermal fogging unit (500-600 F, 10 second run time) and found to produce a dry, thick and visible fog having a volume median diameter (VMD) measurement of approximately 4 microns. Obscuration Data illustrating the filler's ability to produce an unexpected increase in fog visibility is illustrated in Table 2 below (results shown relative to a control composition (10% fludioxonil in Dowanol PM)).

TABLE 2

| | Optical Concentration (Obscuration) | | | |
| --- | --- | --- | --- | --- |
| Formulation | Run 1 | Run 2 | Run 3 | Average |
| Comp. 2 | 44.87 | 27.46 | 24.35 | 32.22667 |
| Control | 12.39 | 8.85 | 5.29 | 8.843333 |

As seen, obscuration was significantly improved by use of the filler. VMD and Obscuration Data was obtained using a using Sympatec HELOS laser diffraction sensor at approximately 1 meter from the exit of the fogger (10 second run time).

EXPERIMENT 4

Application Uniformity

Figure 2:
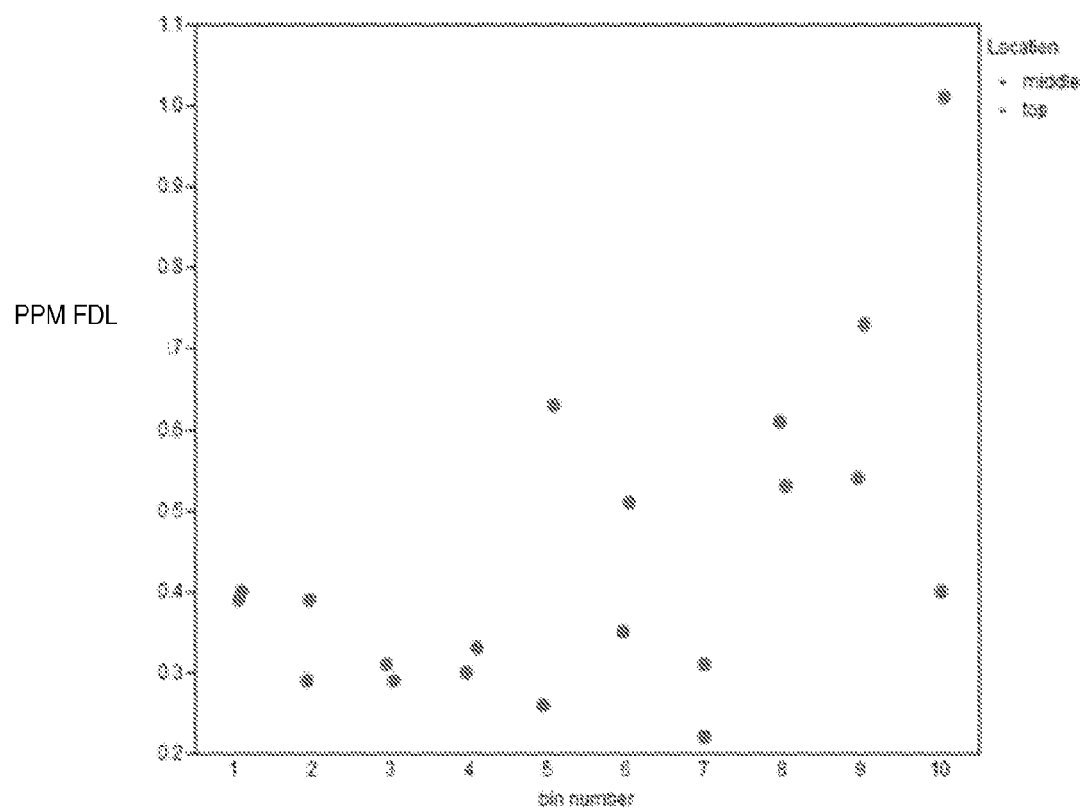

FIG. 1 illustrates a side view of storage container 20 showing the bin configuration used for Experiment 4. Bins 1-10 were filled with pome (approximately 900 lbs/bin) and stacked in the manner illustrated on the floor of the container. A protective tarp 24 was positioned to cover the sides of bins 1 and 5 proximal to fog portal 22 . 124 mL of Composition 2 was fogged (using a Swingtec pulse jet fogger) through portal 22 at a rate of 100 mL/min (rate based on 1 g of FDL/bin+20% excess). Container 22 was sealed following application (2 hours with circulation fans off, then overnight with circulation fans on). FIG. 2 illustrates residue data obtained from fruit located in the middle and on the top of each bin. As seen, using compositions and methods as disclosed herein, even fruit in the middle of covered bins, e.g. bin 2, was treated.

Using methods and systems as described herein, applicants believe the post-harvest treatment of crops, including fruits and vegetables, will be improved. In many embodiments contained herein, formulations disclosed will not be damaging to the post-harvest material. Further, Applicants believe that using methods and systems described herein will improve transport and storage of crops.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an,"

and "the" include plural referents unless expressly and unequivocally limited to one referent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein, and every number between the end points. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10, as well as all ranges beginning and ending within the end points, e.g. 2 to 9, 3 to 8, 3 to 9, 4 to 7, and finally to each number 1, 2, 3, 4, 5, 6, 7, 8, 9 and 10 contained within the range.

What is claimed is:

1. A composition for the post-harvest treatment of crops, the composition comprising:
    about 1% to about 20%, by weight percent, of at least one fungicidally-active compound;
    about 1% to about 80%, by weight percent, of at least one ether solvent; and
    about 5% to about 40%, by weight percent, of at least one filler.

2. The composition of claim 1, wherein the at least one fungicidally active compound includes at least one compound chosen from a triazole derivative, a strobilurin, a carbamate, a benzimidazole, a N-trihalomethylthio compound, a substituted benzene, a carboxamide, a phenylamide, a phenylpyrrole and a succinate dehydrogenase inhibitor.

3. The composition of claim 1, wherein the at least one fungicidally active compound includes at least one compound chosen from fludioxonil, mefenoxam, metalaxyl, difenoconazole, propiconazole, thiabendazole, and azoxystrobin.

4. The composition of claim 1, wherein the at least one ether solvent has
    a boiling point in the range of 130° C. to 200° C. and
    a flash point in the range of 25° C. to 100° C.

5. The composition of claim 1, wherein the ether solvent includes at least one glycol ether solvent.

6. The composition of claim 5, wherein the at least one glycol ether solvent includes propylene glycol methyl ether.

7. The composition of claim 1, wherein the at least one filler includes at least one of 2-ethyl-1-hexanol, alpha-tocopherol, amyl acetate, decyl alcohol, dimethylformamide, dimethylsulfoxide, dipropylene glycol, ethylene glycol, glycerine, hexanol, isopropyl myristate, methyl isobutyl ketone, methyl oleate, N-methyl pyrrolidinone, octanol, oleic acid, oleyl alcohol, propylene glycol, p-xylene, and triacetin.

8. The composition of claim 1, wherein when thermally fogged, the composition produces particles having a volume median diameter (VMD) in the range of 3 to 10 microns.

9. The composition of claim 8, wherein the composition produces particles having a VMD in the range of 3 to 10 microns when thermally fogged at a temperature in the range of 550 ° F. to 750 ° F.

10. A composition for the post-harvest treatment of fruits and vegetables, the composition comprising:
    about 1% to about 20%, by weight percent, of at least one fungicidally-active compound chosen from at least one of fludioxonil, mefenoxam, metalaxyl, difenoconazole, propiconazole, thiabendazole and azoxystrobin;
    about 1% to about 80%, by weight percent, of an ether solvent having thermal fogging capability; and
    about 20% to about 35%, by weight percent, of a filler,
    wherein when exposed to a temperature in the range of 550 ° F. to 750 ° F. in a thermal fogger, the composition produces particles having a VMD in the range of 3 to 10 microns.

11. The composition of claim 10, wherein the filler includes at least one of 2-ethyl-1-hexanol, alpha-tocopherol, amyl acetate, decyl alcohol, dimethylformamide, dimethylsulfoxide, dipropylene glycol, ethylene glycol, glycerine, hexanol, isopropyl myristate, methyl isobutyl ketone, methyl oleate, N-methyl pyrrolidinone, octanol, oleic acid, oleyl alcohol, propylene glycol, p-xylene, triacetin.

12. A method of treating post-harvest crops, the method comprising:
    applying to the post-harvest crops an effective amount of a composition according to claim 1.

13. The method of claim 12, wherein applying includes fogging the composition of claim 1 with a thermal fogger to create a particles having a VMD in the range of 3 to 10 microns.

14. The method of claim 13, wherein the composition is fogged at a temperature in the range of 550 ° F. to 750 ° F.

15. The method of claim 12, wherein the composition is fogged from a ready-to-use formulation, without requiring a dilution step to create the particles having a VMD in the range of 3 to 10 microns.

16. A storage and shipping container comprising a composition as in claim 1.

* * * * *